United States Patent
Watanabe et al.

(10) Patent No.: US 9,933,345 B2
(45) Date of Patent: Apr. 3, 2018

(54) WELDING INSPECTION ROBOT SYSTEM

(71) Applicant: FANUC CORPORATION, Yamanashi (JP)

(72) Inventors: Hideyuki Watanabe, Yamanashi (JP); Masaru Oda, Yamanashi (JP)

(73) Assignee: FANUC CORPORATION, Yamanashi (JP)

(*) Notice: Subject to any disclaimer, the term of this patent is extended or adjusted under 35 U.S.C. 154(b) by 235 days.

(21) Appl. No.: 14/672,384

(22) Filed: Mar. 30, 2015

(65) Prior Publication Data
US 2015/0285721 A1 Oct. 8, 2015

(30) Foreign Application Priority Data

Apr. 2, 2014 (JP) ................. 2014-076423

(51) Int. Cl.
*G01N 3/08* (2006.01)
*G01B 21/00* (2006.01)
*G01M 5/00* (2006.01)

(52) U.S. Cl.
CPC ............... *G01N 3/08* (2013.01); *G01B 21/00* (2013.01); *G01M 5/0075* (2013.01);
(Continued)

(58) Field of Classification Search
CPC .............. G01B 21/00; G01M 5/0075; G01N 2203/0296; G01N 2203/0405; G01N 2203/0482; G01N 2203/0682; G01N 3/08; Y10S 901/42; Y10S 901/46; Y10S 901/02; Y10S 901/31; Y10S 901/32;
(Continued)

(56) References Cited

U.S. PATENT DOCUMENTS 4,579,380 A * 4/1986 Zaremsky ............. B25J 13/082
                                              294/119.1
4,699,414 A * 10/1987 Jones .................... B25J 15/026
                                              294/119.1
(Continued)

FOREIGN PATENT DOCUMENTS

JP     5332906 A    12/1993
JP     8309295 A    11/1996
(Continued)

OTHER PUBLICATIONS

English Abstract for Japanese Publication No. 2007-278809, published Oct. 25, 2007, 1 pg.
(Continued)

*Primary Examiner* — Randy Gibson
*Assistant Examiner* — Gedeon M Kidanu
(74) *Attorney, Agent, or Firm* — Fredrikson & Byron, P.A.

(57) ABSTRACT

The robot system includes a robot having an arm which is provided, on its tip, with two claws which are driven by a servo motor. According to this robot system, a relative position of the two claws is detected when the two claws apply a load of a predetermined force to a welded part welded to a workpiece. The deviation between the detected relative position and a predetermined reference relative position is calculated. The workpiece is determined to be of a good quality or poor quality by comparing the calculated deviation to a predetermined threshold value.

6 Claims, 8 Drawing Sheets

(52) U.S. Cl.
CPC ............... *G01N 2203/0296* (2013.01); *G01N 2203/0405* (2013.01); *G01N 2203/0482* (2013.01); *G01N 2203/0682* (2013.01); *Y10S 901/42* (2013.01); *Y10S 901/46* (2013.01)

(58) Field of Classification Search
CPC ....... Y10S 901/34; Y10S 901/36; B21J 13/10; B25J 15/0028; B25J 15/0061; B25J 15/0253; B25J 19/023; B25J 9/1679; B25J 15/0033; B25J 15/08; B25J 15/0004; B25J 15/0038; B25J 15/0047; B25J 15/10; G05B 15/02; B65G 49/00
See application file for complete search history.

(56) References Cited

U.S. PATENT DOCUMENTS

| | | | |
|---|---|---|---|
| 4,819,978 A | 4/1989 | Scheinman et al. | |
| 8,256,296 B2* | 9/2012 | Ume | G01N 29/11 73/600 |
| 2003/0234239 A1* | 12/2003 | Lee | B23K 11/24 219/109 |
| 2008/0308533 A1* | 12/2008 | Takahashi | B23K 11/253 219/117.1 |
| 2009/0001056 A1* | 1/2009 | Takahashi | B23K 11/315 219/86.7 |
| 2010/0156127 A1* | 6/2010 | De Kervanoael | B25J 15/0253 294/106 |
| 2011/0048650 A1* | 3/2011 | Lawson | B25J 15/0028 157/16 |
| 2011/0180516 A1* | 7/2011 | Takahashi | B23K 11/255 219/86.41 |
| 2011/0208355 A1* | 8/2011 | Tsusaka | B25J 9/1664 700/246 |
| 2011/0270444 A1* | 11/2011 | Nagata | G05B 19/401 700/258 |
| 2013/0259632 A1* | 10/2013 | Watanabe | B65G 49/00 414/800 |
| 2015/0123416 A1* | 5/2015 | Kitamura | B25J 15/0038 294/207 |

FOREIGN PATENT DOCUMENTS

| | | |
|---|---|---|
| JP | 2007278809 A | 10/2007 |
| JP | 201446449 A | 3/2014 |
| JP | 20159253 A | 1/2015 |

OTHER PUBLICATIONS

English Abstract and Machine Translation for Japanese Publication No. 2015-009253 A, published Jan. 19, 2015, 18 pgs.
English Abstract and Machine Translation for Japanese Publication No. 2014-046449 A, published Mar. 17, 2014, 18 pgs.
English Abstract and Machine Translation for Japanese Publication No. 08-309295 A, published Nov. 26, 1996, 8 pgs.
English Abstract and Machine Translation for Japanese Publication No. 05-332906 A, published Dec. 17, 1993, 7 pgs.

\* cited by examiner

WELDING INSPECTION ROBOT SYSTEM

BACKGROUND ART

1. Technical Field

The present invention relates to a robot system which performs welding inspection.

2. Description of the Related Art

A robot system which inspects the quality of welds of a welded part welded to a workpiece is well known. For example, JP 2007-278809A discloses a method wherein an ultrasound sensor provided at the tip of a robotic arm is used to inspect the quality of welds.

However, the related art disclosed in JP2007-278809A requires an ultrasound sensor and a sensor control device to control the sensor and therefore the structure is complicated.

Thus, there is a demand for a robot system which has a simple structure which can inspect the quality of welds of a welded part welded to a workpiece.

SUMMARY OF THE INVENTION

According to a first aspect of the present invention, there is provided a robot system for performing welding inspection on a workpiece including a welded part welded thereto, the robot system comprising: a robot including, at a tip of an arm, two claws which are driven by a servo motor; a position detection part which detects a relative position of the two claws when the two claws apply a load of a predetermined force on the welded part; a deviation calculation part which calculates a deviation between the relative position and a predetermined reference relative position; and a determination part which determines that the workpiece is of a good quality when the deviation is not greater than a predetermined threshold value and determines that the workpiece is of a poor quality when the deviation is greater than the threshold value.

According to a second aspect of the present invention, the robot system according to the first aspect further comprises a setting modification part which modifies at least one of magnitude of the force of the load applied to the workpiece, the reference relative position, and the threshold value, according to a type of workpiece.

According to a third aspect of the present invention, there is provided a robot system (10) for performing welding inspection on a workpiece (50) including a welded part (54) welded thereto, the robot system (10) comprising: a robot (20) including, at a tip of an arm, two claws (32) which are driven by a servo motor (34); a position detection part (60) which detects a first relative position of the two claws (32) in which the two claws (32) each contact the welded part (54), and a second relative position of the two claws (32) in which the two claws (32) apply a load of a predetermined force to the welded part (54); an amount of change calculation part (72) which calculates an amount of change between the first relative position and the second relative position; a deviation calculation part (62) which calculates a deviation between the amount of change and a predetermined reference amount of change; and a determination part (64) which determines that the workpiece (50) is of a good quality when the deviation is not greater than a predetermined threshold value and determines that the workpiece (50) is of a poor quality when the deviation is greater than the threshold value.

According to a fourth aspect of the present invention, the robot system of the third aspect further comprises a setting modification part (70) which modifies at least one of magnitude of the force of the load applied to the workpiece (54), the reference relative position, and the threshold value, according to a type of workpiece (50).

According to a fifth aspect of the present invention, the robot system according to any of the first to fourth aspects further comprises a conveyance control part which controls the robot such that the workpiece is held by the two claws, and transported to a specified place, wherein the conveyance control part is configured to control the robot so as to transport a workpiece which has been determined to be of a good quality to a first place, and transport a workpiece which has been determined to be of a poor quality to a second place which is different from the first place.

According to a sixth aspect of the present invention, the robot system according to any of the first to fifth aspects further comprises an opening width adjuster which adjusts an opening width of the two claws before and after applying a load to the welded part according to a type of workpiece.

The objects, features, and advantages of the present invention will become more apparent from the following detailed description of the exemplary embodiments of the present invention illustrated in the accompanying drawings.

DETAILED DESCRIPTION OF THE INVENTION

Figure 1:
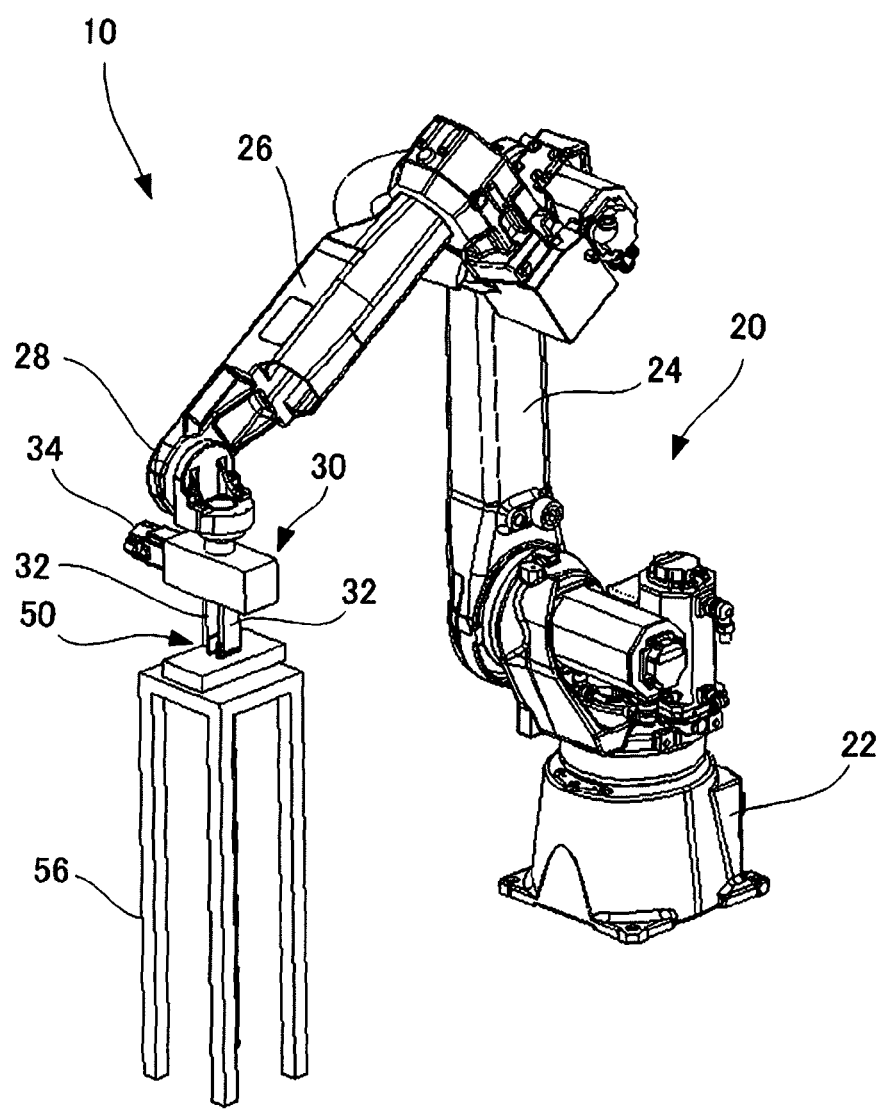
FIG. 1 is a perspective view illustrating an overall configuration of a robot system according to one embodiment.

Hereinafter, embodiments of the present invention will be described referring to the drawings. Constituent elements of the illustrated embodiments may be modified in size in relation to one another, as necessary so as to facilitate the understanding of the present inventions. Further, the same reference numbers for the same or corresponding constituent elements are used over the drawings.

FIG. 1 illustrates a perspective view of an overall configuration of a robot system 10 according to one embodiment. The robot system 10 is a weld inspecting robot system for inspecting the weld quality of a welded part welded onto a workpiece. The robot system 10 includes a robot 20 which is controlled by a robot control device (not shown).

The robot 20 includes a base 22 having a rotatable body part, a lower arm 24 rotatably fitted to the base 22, an upper arm 26 rotatably fitted to the lower arm 24, a wrist part 28 rotatably fitted to the upper arm 26, and a hand 30 fitted to the wrist part 28. The robot 20 exemplified in FIG. 1 has six axes, but the present invention can be applied to any type of robot.

The hand 30 is provided with a pair of claws 32 which protrude and extend from the hand 30, and which are relatively movable to come toward or away from each other. The claws 32 are controlled by a servo motor 34 so as to have any desired opening width within its range of motion. The claws 32 of the hand 30 are controlled so as to apply a load of a predetermined force to the welded part when performing welding inspection.

Figure 2:
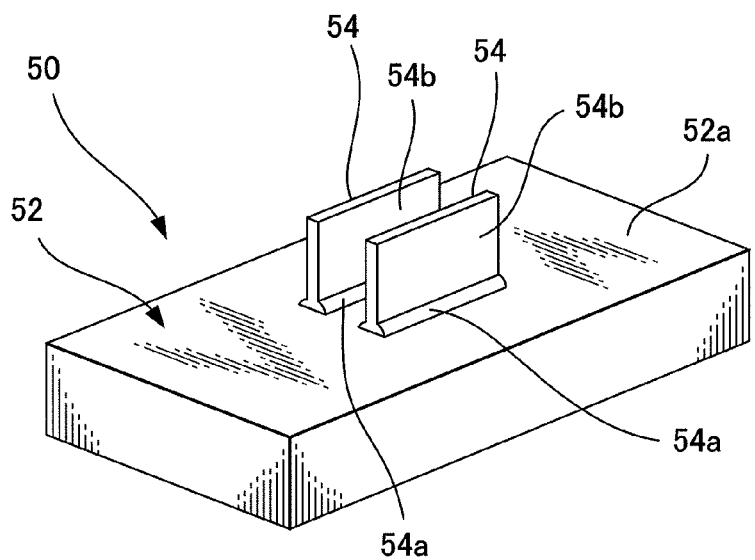
FIG. 2 is perspective view illustrating a workpiece on which welding inspection is to be performed.

FIG. 2 is a perspective view illustrating a workpiece 50 on which welding inspection is to be performed. The workpiece 50 has a substantially rectangular parallelepiped main body 52 and two welded parts 54 which are welded to the upper surface 52a of the main body 52. Each welded part 54 has a base part 54a which is welded to the workpiece 50 and a plate-like flat board part 54b extending from the base part 54a away from the upper surface 52a of the main body 52. The base part 54a of the welded part 54 is welded to the main body 52 by a well known welding method such as spot welding or laser welding. The welded parts 54 are fixed such that the flat board parts 54b extend in parallel with each other. The illustrated workpiece 50 is just one example and a person skilled in the art would be able to recognize that the present invention may be used to perform welding inspection on workpieces having other forms.

Figure 3A:
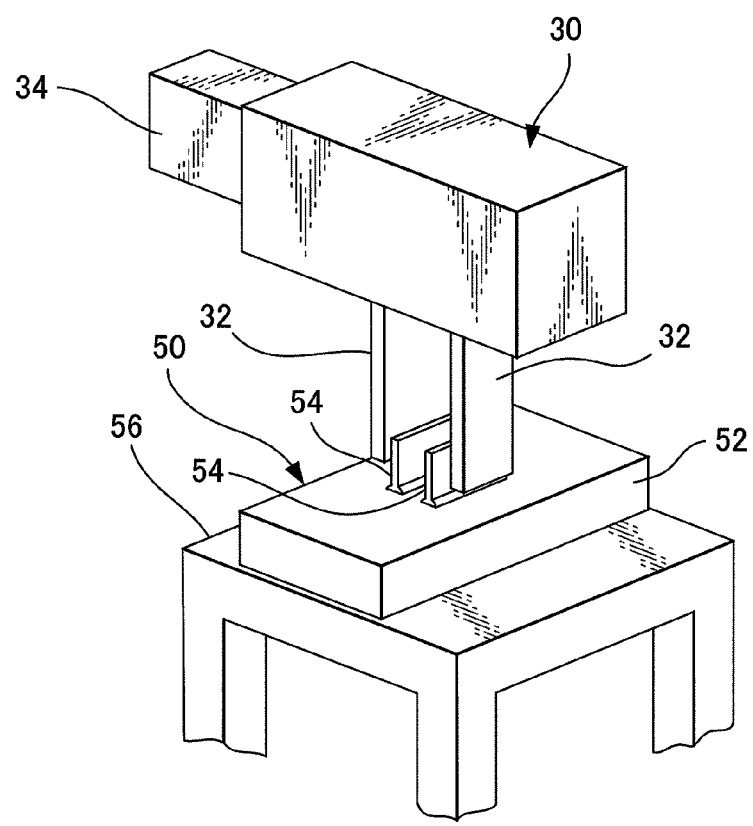
FIG. 3A is a partially enlarged view illustrating the surrounding of the workpiece.
Figure 3B:
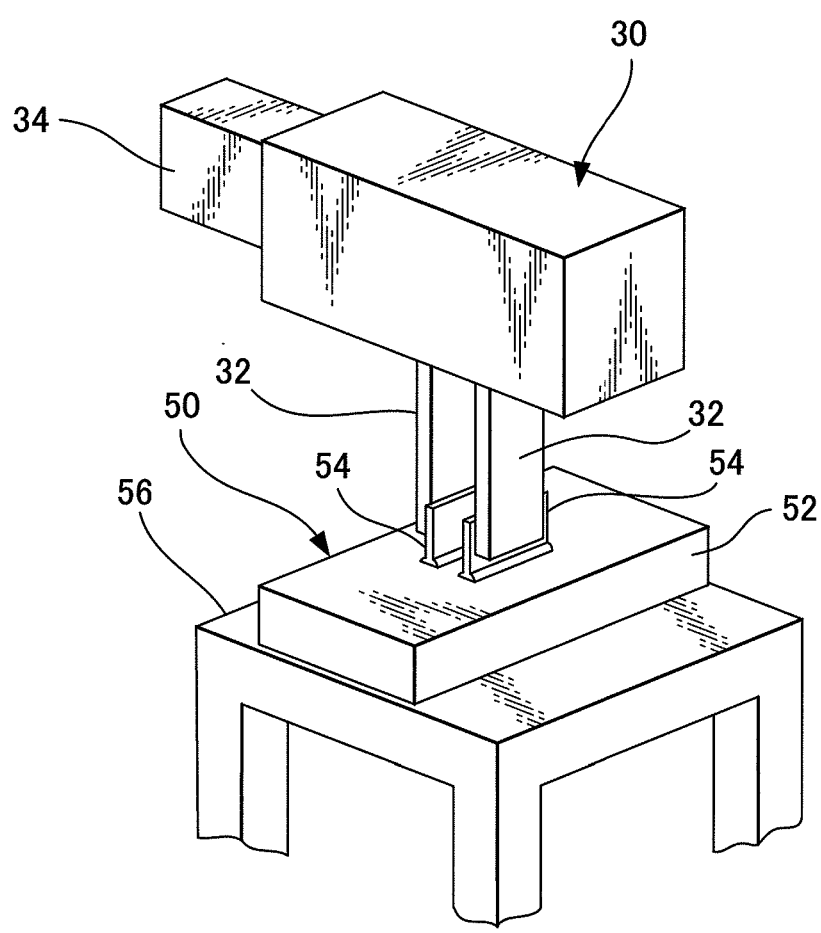
FIG. 3B is a partially enlarged view illustrating the surrounding of the workpiece.

FIGS. 3A and 3B are partially enlarged views of the surrounding of the workpiece 50. Firstly, as shown in FIG. 3A, when welding inspection is being performed, the robot 20 moves the hand 30 to a predetermined position with respect to the workpiece 50 which is mounted on a work bench 56. At this time, the hand 30 is positioned such that the welded parts 54 are each disposed between the claws 32 of the hand 30.

Further, as shown in FIG. 3B, the claws 32 of the hand 30 are moved in a closing direction to come toward each other. At this time the servo motor 34 which drives the claws 32 is controlled to rotate at a predetermined torque. The torque is determined in accordance with the load to be applied to the welded part 54 while performing welding inspection. The claws 32 are driven in the closing direction to contact the surface of the flat board parts 54b of the welded parts 54, and further to apply a load to the welded parts 54 at a predetermined force corresponding to the magnitude of the torque.

Figure 4:
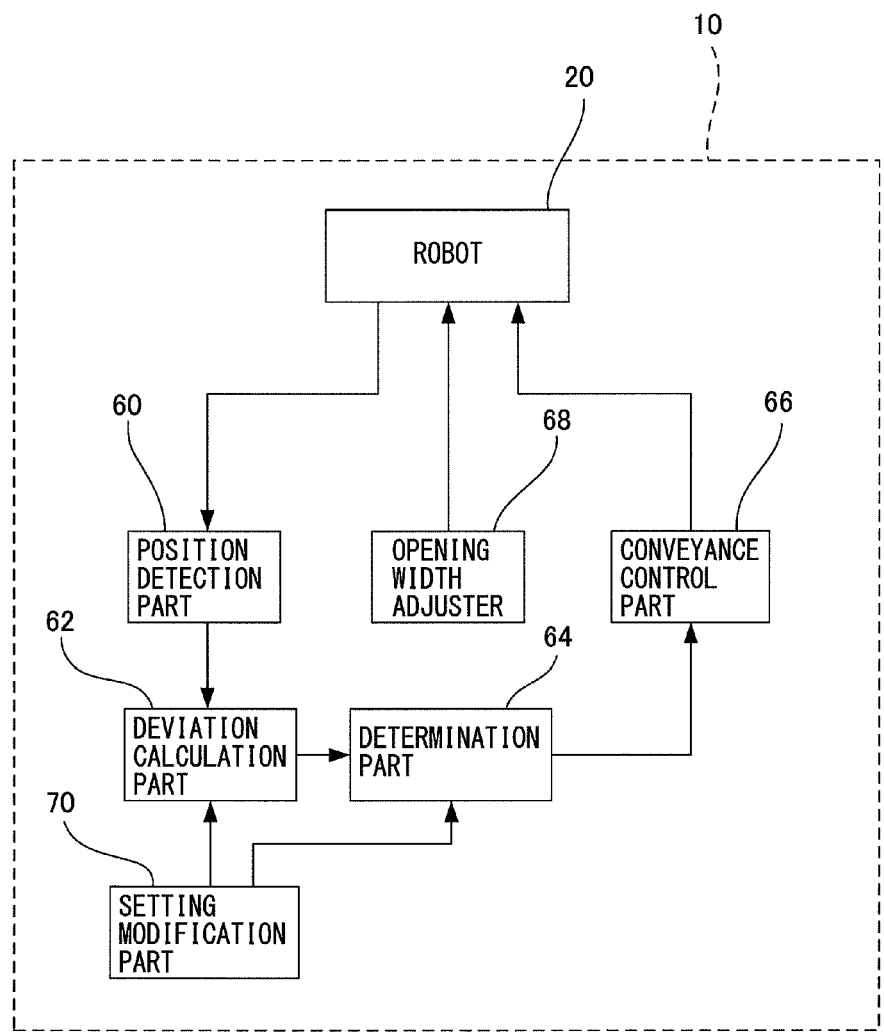
FIG. 4 is a functional block diagram of the robot system according to one embodiment.

FIG. 4 shows a functional block diagram of the robot system 10 according to one embodiment. As illustrated, the robot system 10 includes a position detection part 60, a deviation calculation part 62, a determination part 64, a conveyance control part 66, an opening width adjuster 68, and a setting modification part 70.

The position detection part 60 detects the relative position of the two claws 32. In this embodiment, the claws 32 are driven to open and close by the servo motor 34. Therefore, the relative position of the claws 32 can be detected by for example, detecting the rotational position of the servo motor 34. The rotational position of the servo motor can be detected by for example, a rotary encoder. The position detection part 60 is configured so as to detect the relative position of the claws 32 when a load is applied to the welded parts 54 at a predetermined force by the claws 32 during welding inspection. The relative position of the claws 32 is outputted to the deviation calculation part 62 from the position detection part 60.

The deviation calculation part 62 calculates the deviation between the relative position of the claws 32 detected by the position detection part 60 and a predetermined reference relative position. The reference relative position is for example, a relative position of the claws 32 obtained when a load is applied to a workpiece 50 which has passed the welding inspection under the same conditions. Therefore, the reference relative position can be determined empirically. The deviation calculated by the deviation calculation part 62 is outputted to the determination part 64.

The determination part 64 compares the deviation calculated by the deviation calculation part 62 and a predetermined threshold value to determine that, when the deviation is not greater than the threshold value, the workpiece 50 is of a good quality. On the other hand, the workpiece 50 is determined to be of a poor quality when the deviation calculated by the deviation calculation part 62 is greater than the threshold value. The result of the determination is outputted to the conveyance control part 66.

The conveyance control part 66 controls the robot 20 so as to convey the workpiece 50 which has completed the welding inspection to a specified target position corresponding to the result of the inspection. A workpiece 50 which is determined to be of a good quality may be transported to for example, a conveyor such that the workpiece may undergo further processing. On the other hand, a workpiece which is determined to be of a poor quality may be transported to for example, a conveyor such that the workpiece is scrapped or recycled.

Figure 5:
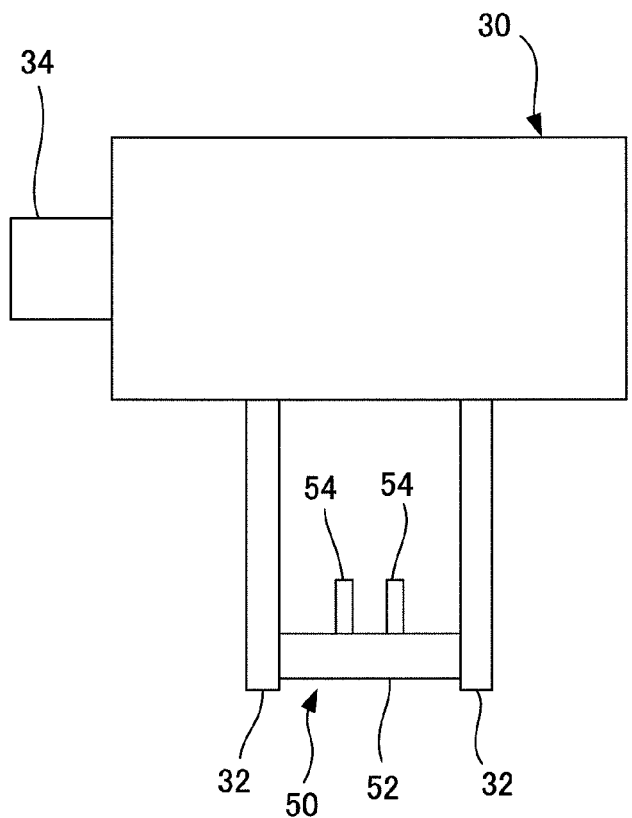
FIG. 5 is a side view illustrating the workpiece held by a hand for transportation.

At this time, the hand 30 which has been used for the welding inspection may also be used for transporting the workpiece 50. FIG. 5 is a side view showing the hand 30 which is holding the workpiece 50 to transport the workpiece 50. As illustrated, the hand 30 expands the opening width of the claws 32 more than when performing the welding inspection, and therefore the main body 52 of the workpiece 50 can be stably held. In this way, the configuration of the robot system 10 can be simplified by using the same hand 30 for the purpose of transporting the workpiece 50.

The setting modification part 70 can modify the magnitude of the force applied as a load to the welded parts 54 by the claws 32, the reference relative position, or the threshold value used by the determination part 64 for determining the quality of the workpiece, according to the type of workpiece. The strength of the welded part 54 of the workpiece 50 varies depending on the type of weld, the dimensions of the base part 54a of the welded part 54, the materials and other factors. Further, the required strength of the welded part may vary depending on its usage. Therefore, each of the values to be modified by the setting modification part 70 can be empirically obtained based on the type of workpiece 50.

The opening width adjuster 68 adjusts the opening width of the claws 32 before and after applying a load to the welded part 54. The opening width of the claws 32 can be set arbitrarily by changing the rotational position of the servo motor 34. However, if the opening width of the claws 32 is too large or too small while weld inspection is being performed, the claws 32 may interfere with surrounding objects.

Figure 6:
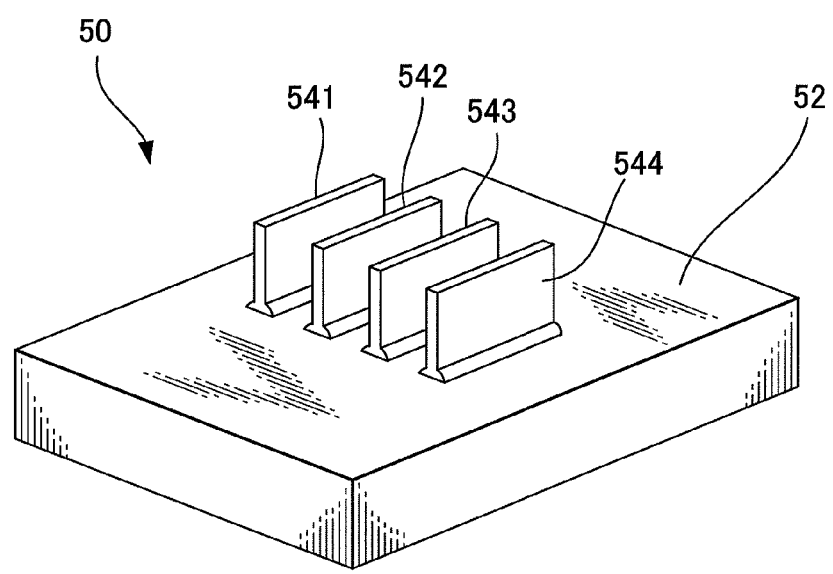
FIG. 6 is a perspective view illustrating a workpiece in another form.

The mode of operation of the opening width adjuster 68 will be explained with reference to FIG. 6 which shows the workpiece 50 in a different form. The workpiece 50 shown in FIG. 6 has four welded parts 541 to 544 welded to the main body 52. In the following example, a load is applied via claws 32, as shown in FIG. 3, to a second welded part 542 and a third welded part 543, which are affixed between a first welded part 541 and a fourth welded part 544 which are positioned on opposite sides. In this case, the two claws 32 of the hand 30 must be positioned such that one claw is positioned between the first welded part 541 and the second welded part 542 and the other claw is positioned between the third welded part 543 and the fourth welded part 544, in order to perform welding inspection. However, if the opening width of the claws 32 is too large, there is a possibility that the claws will interfere with and break the first welded part 541 or the fourth welded part 544. According to the present embodiment, by appropriately setting the opening width of the claws 32 by the opening width adjuster 68 according to the type of workpiece 50, the interference of the claws with the workpiece 50 or the like can be prevented. Further, the opening width adjuster 68 which adjusts the opening width of the claws 32 can be used to determine the position of the claws 32 when releasing the claws 32 from the welded parts 54 after performing welding inspection.

Figure 7:
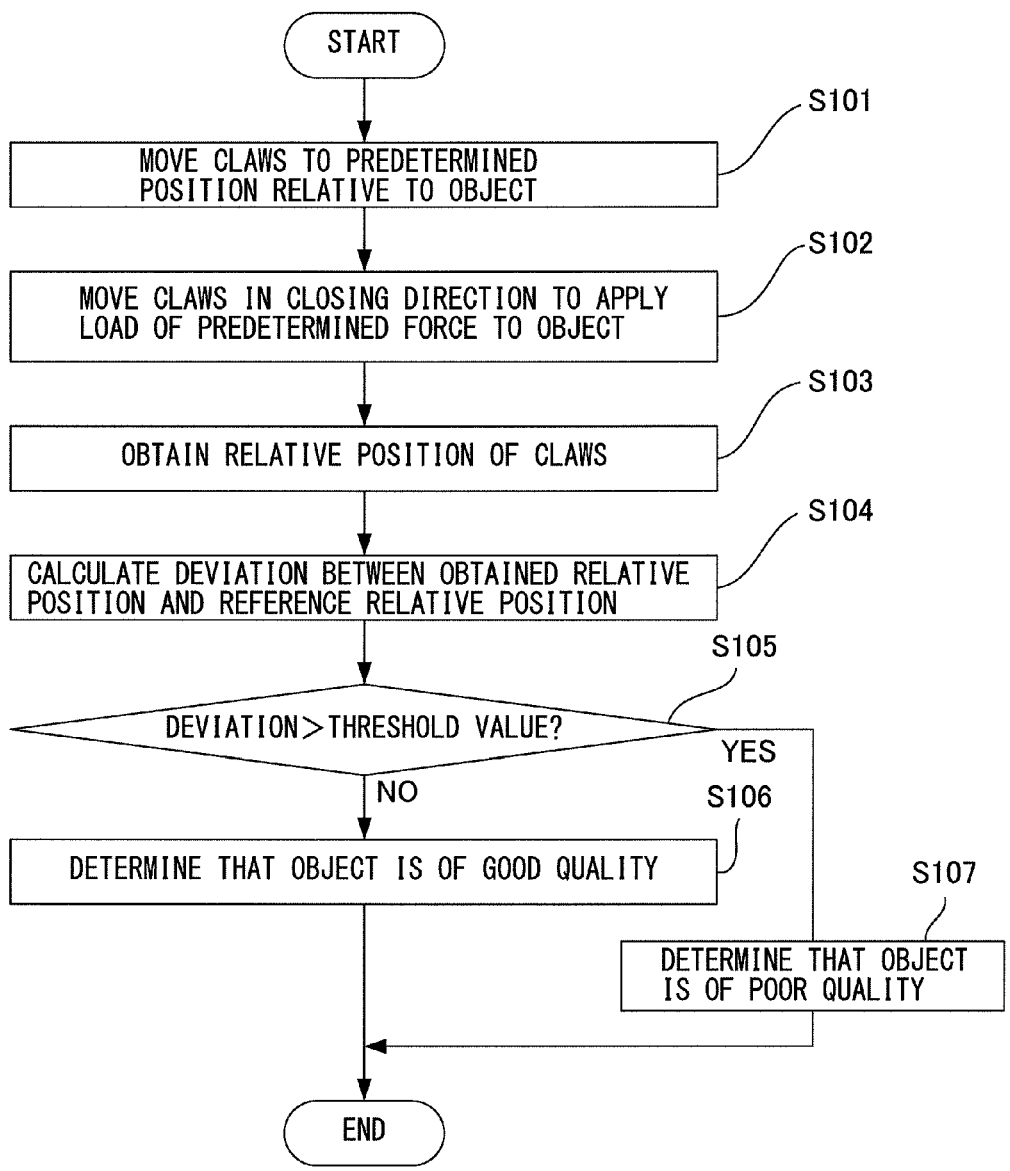
FIG. 7 is a flowchart illustrating the steps to perform welding inspection using the robot system of FIG. 4.

FIG. 7 is a flowchart illustrating the steps involved when performing welding inspection using the robot system 10 of FIG. 4. Firstly, at step S101, the robot 20 is controlled to position the hand 30 such that the welded parts 54 of the workpiece 50 to be inspected are positioned between the claws 32. The opening width of the claws 32 may be the width which has been adjusted by the opening width adjuster 68.

Next, at step 102, the claws 32 are driven in a closing direction by rotating the servomotor 34 with a predetermined torque, to apply a load to the welded parts 54 of the workpiece 50. The magnitude of the torque can be determined empirically in accordance with the magnitude of the force necessary to apply the load to the welded parts 54. For example, the magnitude of the load may be set such that an elastic deformation of the welded parts 54 of the workpiece 50 occurs, but a plastic deformation thereof does not occur.

At step 103, a relative position of claws 32 is obtained by the position detection part 60 while the load is being applied to the welded parts 54. At step S104, the deviation calculation part 62 calculates a deviation between the relative position of the claws 32 obtained in the previous step and a reference relative position.

At step S105, the determination part 64 determines whether the quality of the workpiece 50 is good or poor by comparing the deviation calculated at step S104 by and a predetermined threshold value. Specifically, when the deviation is not greater than the threshold value, the control proceeds to step S106 at which the quality of the workpiece is determined to be good. On the other hand, if the deviation is greater than the threshold value, the control proceeds to step S107 at which the quality of the workpiece is determined to be poor.

Following steps S106 and S107, the conveyance control part 66 may control the robot 20 to transport the workpiece 50 to different sites individually, depending on whether its quality is good or poor, although this is not illustrated in FIG. 7.

According to the robot system of the present embodiments, the following effects may be obtained.

(1) Welding inspection is performed based on the displacement amount of the welded part when a load of a predetermined force is applied via the claws of the hand. Therefore, the configuration of the robot system can be simplified as a special sensor for inspecting a weld and a control unit therefor are not necessary.

(2) Since a hand controlled by a servo motor is used for performing the welding inspection, the conditions for inspecting a weld can be appropriately modified according to the type of workpiece. Further, if the hand is driven by a servo motor, the opening width of the claws can be modified as necessary before and after applying a load to the workpiece and therefore the claws can be prevented from interfering with surrounding objects before and after welding inspection is performed.

(3) The configuration of the robot system can be simplified as the hand is commonly used both for performing the weld inspection and for transporting the workpiece. In particular, miniaturization of the hand can be realized.

Figure 8:
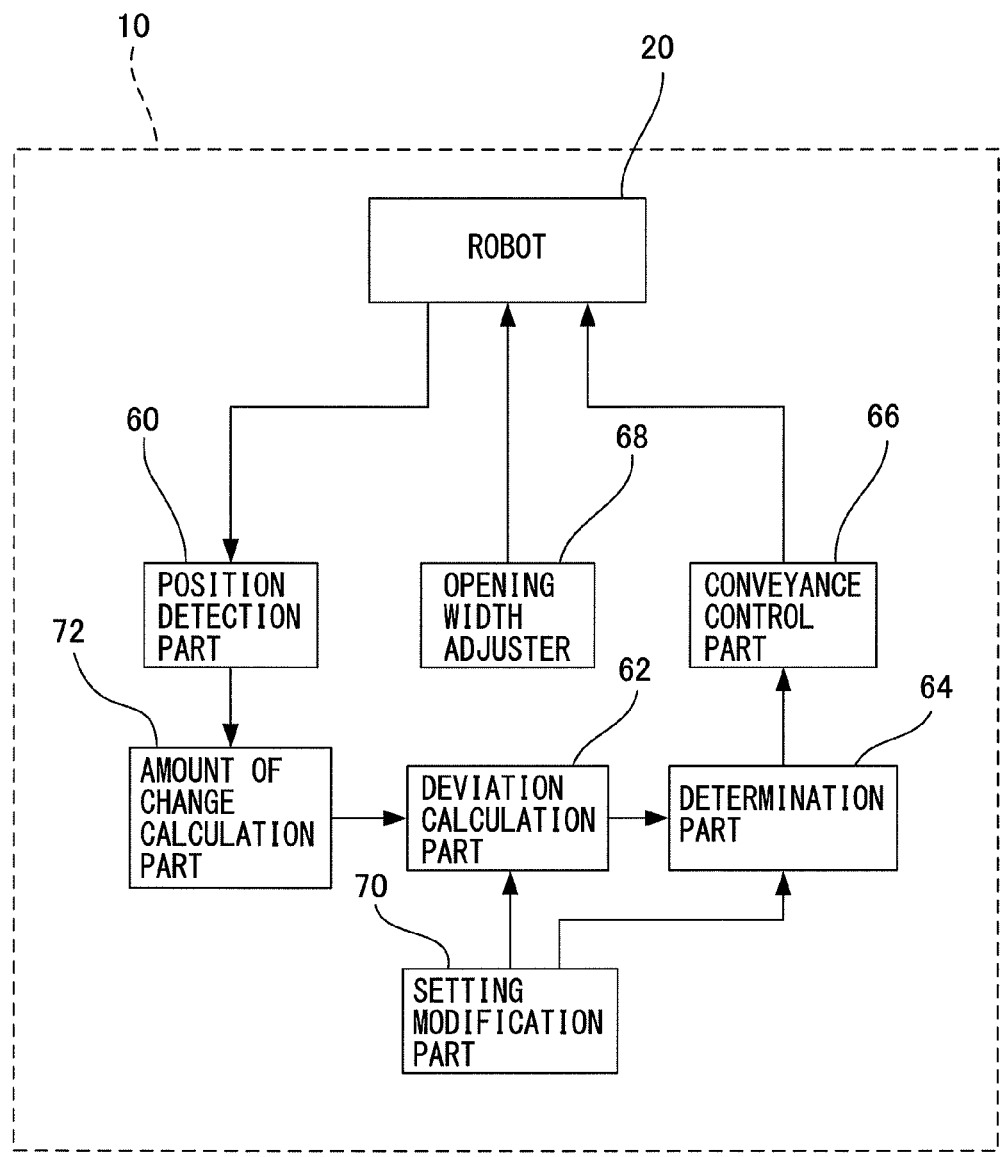
FIG. 8 is a functional block diagram of the robot system according to another embodiment.

FIG. 8 is a functional block diagram of a robot system 10 according to another embodiment. Compared to FIG. 4, the robot system 10 of this embodiment further includes an amount of change calculation part 72. According to this embodiment, the position detection part 60 is configured to obtain the relative position of the claws 32 in two separate steps.

Namely, the position detection part 60 obtains the relative position of the claws 32 when the claws 32 contact the welded parts 54 prior to applying a load to the welded parts 54 (hereinafter referred to as "the first relative position"). The position detection part 60 also obtains the relative position of the claws 32 when a load is applied to the welded part 54 at a predetermined force (hereinafter referred to as "the second relative position").

The amount of change calculation part 72 calculates the amount of change between the first relative position and the second relative position. Namely, the amount of change which is calculated by the amount of change calculation part 72 corresponds to the displacement amount of the welded parts 54 before and after the load is applied.

Figure 9:
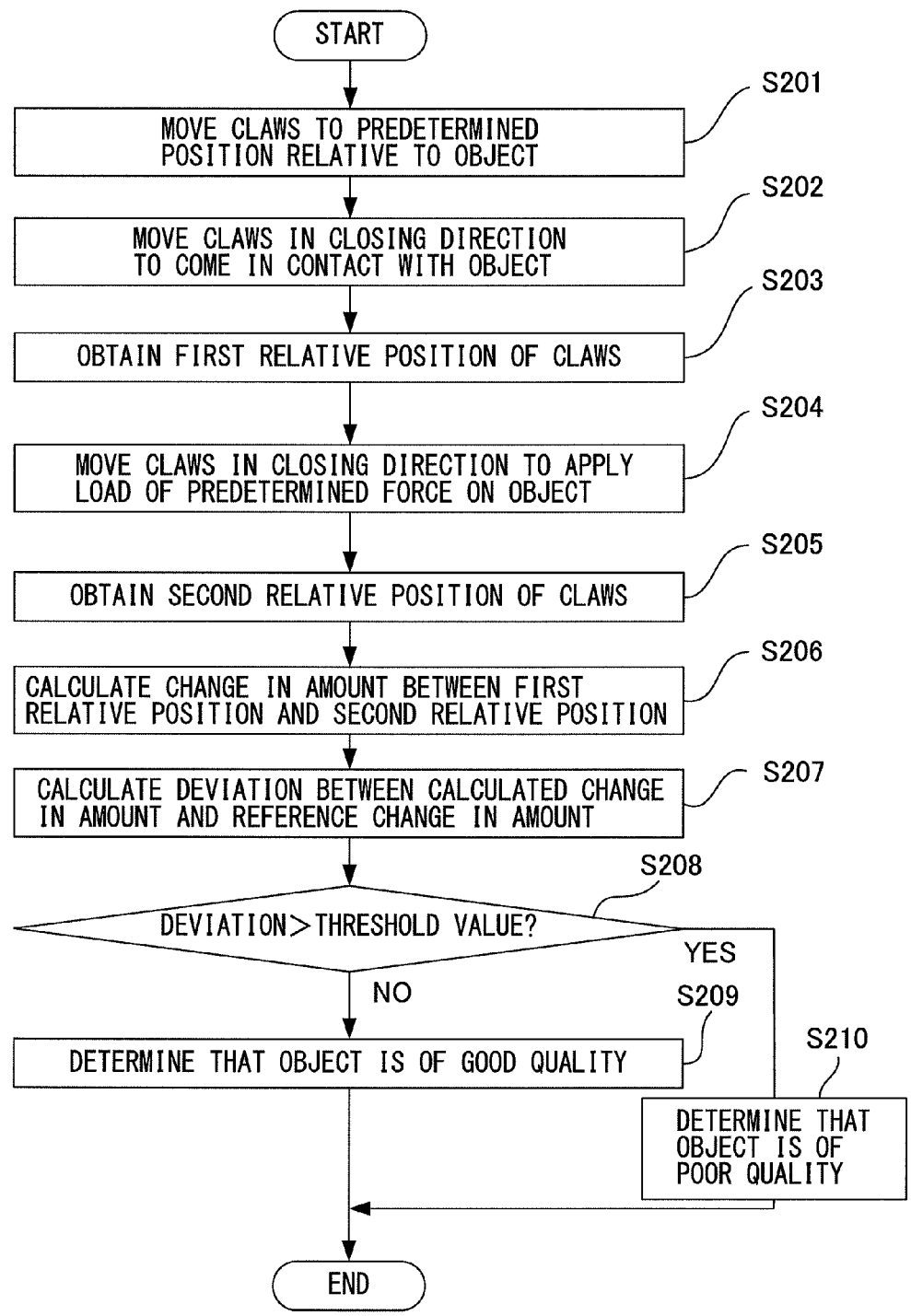
FIG. 9 is a flow chart illustrating the steps to perform weld inspection using the robot system of FIG. 8.

FIG. 9 is a flowchart which shows the steps of welding inspection performed by the robot system of FIG. 8. Firstly, at step S201, the robot 20 is controlled to position the claws 32 relative to the welded parts 54. Next, at step S202, the claws 32 are driven in a closing direction by rotating the servo motor 34 until the claws 32 contact the welded parts 54. At step S203, the first relative position is obtained by the position detection part 60.

At step S204, the claws 32 are further driven in the closing direction to apply a load on the welded parts 54 at a predetermined force. At step S205, the position detection part 60 obtains the relative position of the claws 32 with the load applied to the welded parts 54, or in other words, the second relative position.

At step S206, the amount of change calculation part 72 calculates the amount of change between the first relative position and the second relative position. Further, at step S207, the deviation calculation part 62 calculates the deviation between the amount of change calculated by the amount of change calculation part 72 and a predetermined reference amount of change. The reference amount of change is, for example, the amount of change between the first relative position and the second relative position when a load is applied on a workpiece which has passed the welding inspection under the same conditions as the welding inspection.

At step S208, the determination part 64 determines whether the workpiece 50 is of a good quality or poor quality by comparing the deviation calculated at step S207 with a threshold value. Namely, if the deviation is greater than the threshold value, the control proceeds to step S210 at which the quality of the workpiece is determined to be poor. On the other hand, if the deviation is not greater than the threshold value, the control proceeds to step S209, at which the quality of the workpiece is determined to be good.

Further, as described in the previous embodiment, in this embodiment, the adjustment can be made by the opening width adjuster 68 and the setting modification part 70 according to the type of workpiece 50. It should be noted that in this embodiment, the setting modification part 70 is configured to modify, for example, the magnitude of the force corresponding to the load to be applied on the welded parts 54 of the workpiece 50, the reference amount of change and the threshold value, etc.

It would be apparent that the same effects (1) to (3) as in the previously described embodiment can be obtained by the robot system 10 according to this embodiment.

Effects of the Invention

According to the robot system having the aforementioned configuration, the quality of a weld can be determined based on the displacement amount of the welded parts when a predetermined load is applied to the welded parts. This eliminates the need for a specific sensor for inspecting welding quality and a control system therefor, and therefore the configuration of the robot system can be simplified.

Although various embodiments and variants of the present invention have been described above, it is apparent for a person skilled in the art that the intended functions and effects can also be realized by other embodiments and variants. In particular, it is possible to omit or replace a constituent element of the embodiments and variants, or additionally provide a known means, without departing from the scope of the present invention. Further, it is apparent for a person skilled in the art that the present invention can be implemented by any combination of features of the embodiments either explicitly or implicitly disclosed herein.

What is claimed is:

1. A robot system for performing welding inspection on a workpiece including a welded part welded thereto, the robot system comprising:
    a robot including, at a tip of an arm, two claws which are driven by a servo motor;
    a position detection part which detects a first relative position of the two claws in which the two claws each contact the welded part, and a second relative position of the two claws in which the two claws apply a load of a predetermined force to the welded part after contacting the welded part;
    an amount of change calculation part which calculates an amount of change between the first relative position and the second relative position;
    a deviation calculation part which calculates a deviation between the amount of change and a predetermined reference amount of change; and
    a determination part which determines that the workpiece is of a good quality when the deviation is not greater than a predetermined threshold value and determines that the workpiece is of a poor quality when the deviation is greater than the threshold value.

2. The robot system according to claim 1, further comprising a conveyance control part which controls the robot such that the workpiece is held by the two claws, and transported to a specified place,
    wherein the conveyance control part is configured to control the robot so as to transport a workpiece which has been determined to be of a good quality to a first place, and transport a workpiece which has been determined to be of a poor quality to a second place which is different from the first place.

3. The robot system according to claim 1, further comprising an opening width adjuster which adjusts an opening width of the two claws before and after applying a load to the welded part according to a type of workpiece.

4. The robot system according to claim 1, further comprising a setting modification part which modifies at least one of magnitude of the force of the load applied to the welded part, the reference relative position, and the threshold value, according to a type of workpiece.

5. The robot system according to claim 4, further comprising a conveyance control part which controls the robot such that the workpiece is held by the two claws, and transported to a specified place,
    wherein the conveyance control part is configured to control the robot so as to transport a workpiece which has been determined to be of a good quality to a first place, and transport a workpiece which has been determined to be of a poor quality to a second place which is different from the first place.

6. The robot system according to claim 4, further comprising an opening width adjuster which adjusts an opening width of the two claws before and after applying a load to the welded part according to a type of workpiece.

* * * * *